United States Patent
Dreibholz et al.

(10) Patent No.: US 7,429,865 B2
(45) Date of Patent: Sep. 30, 2008

(54) METHOD AND SYSTEM FOR ERROR CHECKING AN ELECTROCHEMICAL SENSOR

(75) Inventors: Joerg Dreibholz, Altrip (DE); Sylvia Saecker, Bensheim (DE); Volker Unkrig, Ladenburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/542,701

(22) Filed: Oct. 4, 2006

(65) Prior Publication Data

US 2007/0102292 A1    May 10, 2007

(30) Foreign Application Priority Data

Oct. 5, 2005    (EP) ................. 05021853

(51) Int. Cl.
*G01R 27/08* (2006.01)
*G01N 27/416* (2006.01)

(52) U.S. Cl. .......... 324/692; 324/439; 324/444; 204/401; 205/792

(58) Field of Classification Search ........... 324/692, 324/439, 444; 204/401; 205/792
See application file for complete search history.

(56) References Cited

U.S. PATENT DOCUMENTS

| | | | |
|---|---|---|---|
| 4,822,456 A | 4/1989 | Bryan | |
| 5,352,351 A | 10/1994 | White et al. | |
| 6,088,608 A | 7/2000 | Schulman et al. | |
| 6,733,655 B1 | 5/2004 | Davies et al. | |
| 6,790,178 B1 | 9/2004 | Mault et al. | |
| 2004/0061919 A1* | 4/2004 | Tench et al. ............. | 359/265 |
| 2005/0263409 A1* | 12/2005 | Song ...................... | 205/787 |
| 2005/0279647 A1* | 12/2005 | Beaty ..................... | 205/792 |

FOREIGN PATENT DOCUMENTS

| | | |
|---|---|---|
| EP | 1 443 322 A1 | 4/2004 |
| EP | 1 455 182 A1 | 8/2004 |
| WO | WP93/08477 | 4/1993 |
| WO | WO01/75438 A2 | 10/2001 |
| WO | WO 03/095092 A1 | 11/2003 |
| WO | WO 2004/113917 A2 | 12/2004 |
| WO | WO 2005/078437 A1 | 8/2005 |

\* cited by examiner

*Primary Examiner*—Vincent Q Nguyen
(74) *Attorney, Agent, or Firm*—Dinsmore & Shohl LLP (57) ABSTRACT

A method and a corresponding system for error checking an electrochemical sensor having at least two electrodes and a liquid measuring medium applied thereto are disclosed. The method involves determining a first admittance between a first set of electrodes of the sensor; determining a second admittance between a second set of electrodes of the sensor; determining a value using the first admittance and the second admittance; and displaying an error message if the value is out of a predetermined tolerance.

18 Claims, 6 Drawing Sheets

METHOD AND SYSTEM FOR ERROR CHECKING AN ELECTROCHEMICAL SENSOR

FIELD OF THE INVENTION

The present invention relates generally to electrochemical sensors, and more particularly to a method and a corresponding system for error checking an electrochemical sensor comprising at least two electrodes.

BACKGROUND OF THE INVENTION

Diagnostic systems analyzing body fluids such as whole blood, plasma, serum, urine, etc., use test carriers (such as test strips, cassettes etc.) to take up a fluid sample to be examined. Such test carriers usually have a sample application site and a measuring chamber that is spatially separated therefrom. The structure of the test carrier must ensure that the sample is transported from the sample application site to the measuring chamber and that the latter is adequately filled with sample liquid. Capillaries can for example be used for this liquid transport as they are described for example in WO 03/095092 or WO 2004/113917.

The measuring chamber usually comprises a detection zone which has a defined geometry and a defined surface. Deviations in the dimensions lead to deviations in the measuring result.

Plastic materials such as foils or injection molded parts which enable a cost-effective manufacture are usually used to manufacture the test carriers. These plastic materials must be joined together during production by adhesively bonding, welding or injection molding processes. In doing so there is a risk that the geometry of the detection zone in the measuring chamber deviates from the specifications for individual test carriers. These deviations can occur during manufacture for example as a result of adhesive exuding into the measuring chamber during manufacture or they may be due to welding or bonding conditions that deviate from the specifications. It is, however, also possible that test carriers become deformed due to mechanical or thermal stress after manufacture resulting in a change in the detection surface in the measuring chamber. Furthermore, it is conceivable that the electrode surface itself was not manufactured in the intended geometric dimensions or was changed by subsequent damage.

Finally, the detection surface can be altered by incomplete filling with sample liquid, by the inclusion of air bubbles in the sample liquid or by a leaky measuring chamber.

In order to check for manufacturing defects in electrochemical blood glucose sensors that run on direct voltage or to check for inadequate covering of the electrodes with sample, U.S. Pat. No. 6,733,655 (Davies et al.) proposes that two independent working electrodes are provided on a test strip which together with a reference electrode that is used in common, result in two sensors. The two sensor parts are measured with respect to the concentration of the substance in the sample (thus in the case of glucose sensors the glucose content of the sample is measured twice in parallel) and the two measured values are compared with one another. If both measured values are the same, it is assumed that the sensor is basically all right. If the measured values differ considerably than an error is assumed.

A disadvantage of this method is that the actual measurement process is used as a control. Thus especially in the case of lengthy measurements (e.g., in the field of coagulation diagnostics) it may take a relatively long time until it is known whether a sensor is OK or not. Defects in parts of the measurement set-up that are identical for both sensor channels (e.g., scratches in the reference electrode etc.) are not detected since they have equal effects on both channels.

U.S. Pat. No. 5,352,351 (White et al.) describes methods for determining the coverage of a measuring surface by sample liquid in electrochemical blood glucose sensors and for monitoring the measuring process. For this purpose discrete direct voltages which differ with respect to time are applied to the electrodes of corresponding sensors and conclusions are drawn from the measured currents.

The method according to U.S. Pat. No. 5,352,351 has basically the same disadvantages as U.S. Pat. No. 6,733,655.

In the prior art there is a lack of methods which would enable the above-mentioned problems to be reliably detected and thus avoid erroneous measurements or to flag such measurements as erroneous.

SUMMARY OF THE INVENTION

The present invention addresses the above mentioned disadvantages of the prior art. In particular, the present invention provides a method and a system that can be used to reliably detect defective electrodes or measuring conditions in electrochemical sensor systems.

In a first embodiment of the invention, a method for error checking the electrochemically active surface of electrochemical sensors comprising at least two electrodes is disclosed. The method is advantageously used to detect deviations of the active electrode surface of the sensor electrodes from specified values. For this purpose according to the invention a liquid measuring medium is firstly applied to the sensor and a first admittance between two electrodes (which should be referred to as the first electrode pair) is determined. Concurrently or subsequently, a second admittance between two electrodes (which should be referred as the second electrode pair) of the sensor is determined. The second two electrodes can, depending on the precise design of the method according to the invention, be identical to the first two electrodes or one of the second electrodes can be identical to one of the first electrodes or the two electrode pairs have no common electrode. The first and the second admittance are finally related to one another, and an error message is provided if the relation is out of tolerance.

In another embodiment of the invention, a measuring instrument that is suitable for carrying out the method according to the invention is disclosed. The measuring instrument comprises contacts for connecting electrodes of a sensor, control and measuring electronics to generate test voltages and detect the sensor signals, at least one processor to compare and correlate the sensor signals on the basis of a program carrying out the method according to the invention and an output unit (display, data interface, printer connection etc.).

In still another embodiment of the invention, a system for carrying out the method according to the invention is disclosed comprising at least one electrochemical sensor with at least two electrodes and a measuring instrument according to the above-mentioned subject matter of the invention.

These and other features and advantages of the invention will be more fully understood from the following description of various embodiments of the invention taken together with the accompanying drawings.

BRIEF DESCRIPTION OF THE DRAWINGS

The following detailed description of the embodiments of the present invention can be best understood when read in conjunction with the following drawings, where like structure is indicated with like reference numerals, and in which.

The numerals and abbreviations in the figures denote:
10 electrochemical sensor
12 base foil
14 1st electrode
16 2nd electrode
18 3rd electrode
20 reagent layer
22 spacer
24 recess
26 cover foil
28 vent hole
30 system
32 measuring instrument
34 alternating voltage source
36 contacts
38 control and measuring electronics
40 processor
42 output unit
Ad1 first admittance
Ad2 second admittance
Δ relative deviation of the measured coagulation time from the target value (in %)
I current (in ampere A)
R contact resistance (in ohm)
t measuring time (in seconds s)
A ampere
s second(s)

DETAILED DESCRIPTION

FIGS. 1A-1E depict a construction of an electrochemical sensor (test strip), generally indicated by symbol 10, on the basis of which the method according to the invention can be elucidated. Typical sensors of this type are also known from WO 03/095092 and WO 2004/113917.

The electrochemical sensor 10 consists of a base foil 12 on which the electrodes 14, 16, 18 are firstly applied. Electrodes 14, 16, 18 are typically printed, glued on or generated by sputtering. It is also possible to firstly metallize the entire surface of the foil 12 (e.g., by sputtering or CVD) and subsequently to work out the electrode structures by means of laser ablation or lithographic process. The electrodes and conductor paths can be composed of the same or different materials. Typically the electrodes and conductor paths consist of a noble metal such as gold, platinum, palladium or such like or alloys or other inert materials.

A reagent layer 20 is applied for example by printing, dispensing, knife-coating, slot nozzle coating, etc., and dried in the area which is to receive the sample. The reagent composition essentially depends on the analyte to be measured or sample parameter to be determined and can be accordingly selected or prepared by a person skilled in the art.

After the reagent layer has dried, a spacer 22 which consists of a dielectric material is applied to the base foil 12, the electrodes 14, 16, 18 and the reagent layer 20. The spacer 22 covers those parts of the electrodes that should not come into contact with the sample and leaves those parts of the electrode free which should come into contact with the sample. For this purpose the spacer 22 has a recess 24 in the region of the reagent layer 20. This recess 24 together with the electrode structures in the reagent region defines the effective active electrode surface or a detection zone.

The spacer 22 also leaves areas of the electrodes/conductor paths 14, 16, 18 free at the end of the sensor 10 that is opposite to the reagent layer 20. These areas are used to contact the sensor 10 in the measuring instrument 32, which shown by FIG. 7.

Figure 1A:
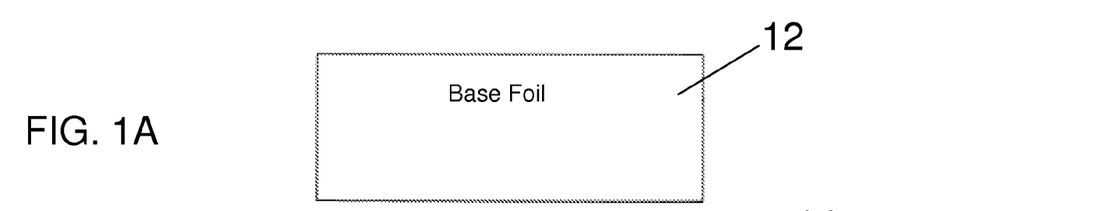
FIGS. 1A-1F show construction of an electrochemical sensor (test strip) on the basis of which the method according to the invention can be elucidated.
Figure 1B:
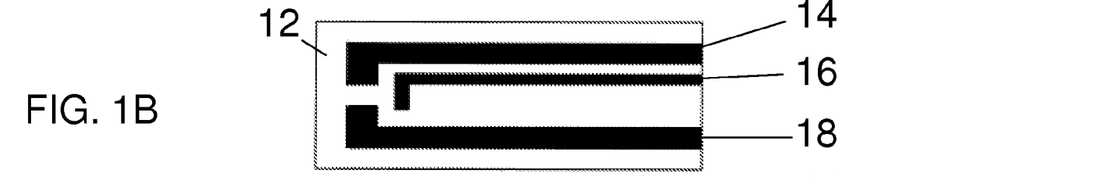
Figure 1C:
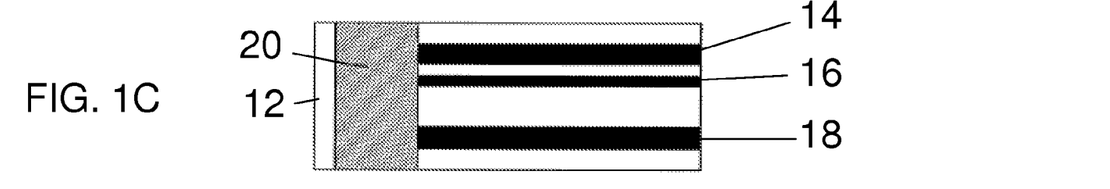
Figure 1D:
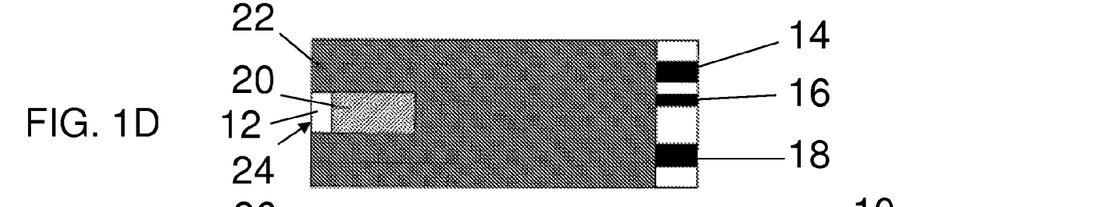

The sensor 10 shown in FIG. 1D would in principle be suitable for carrying out measurements in a liquid media. For example, a sample liquid can be added dropwise from above to the exposed area of the reagent layer 20.

Figure 1E:
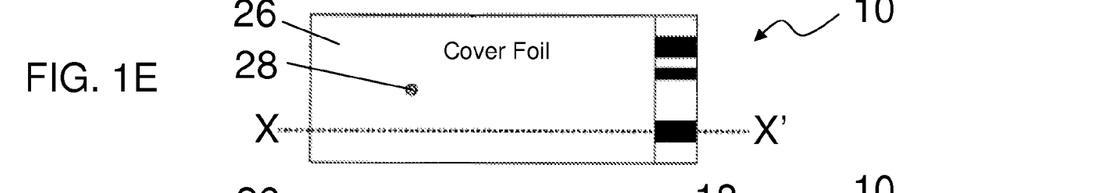

For reasons of hygiene and simple sample dosing, the electrochemical sensors preferably contain a capillary gap/capillary channel. These are generated by applying an additional dielectric foil (cover foil 26) to the spacer 22. If the spacer 22 has a thickness of a few 100 μm or less, a capillary-active gap is thus formed in the area of the recess 24. The sample can now be taken up driven by capillary forces into the sensor 10 from the left side. The air that is displaced in this process can escape from the gap through vent hole 28.

Figure 1F:
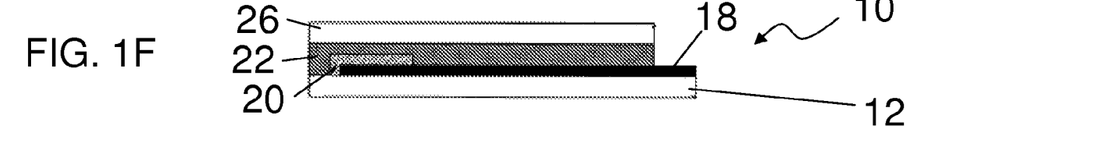

The completely mounted sensor 10 from FIG. 1E is shown in FIG. 1F in a section along the line X-X'.

Figure 8:
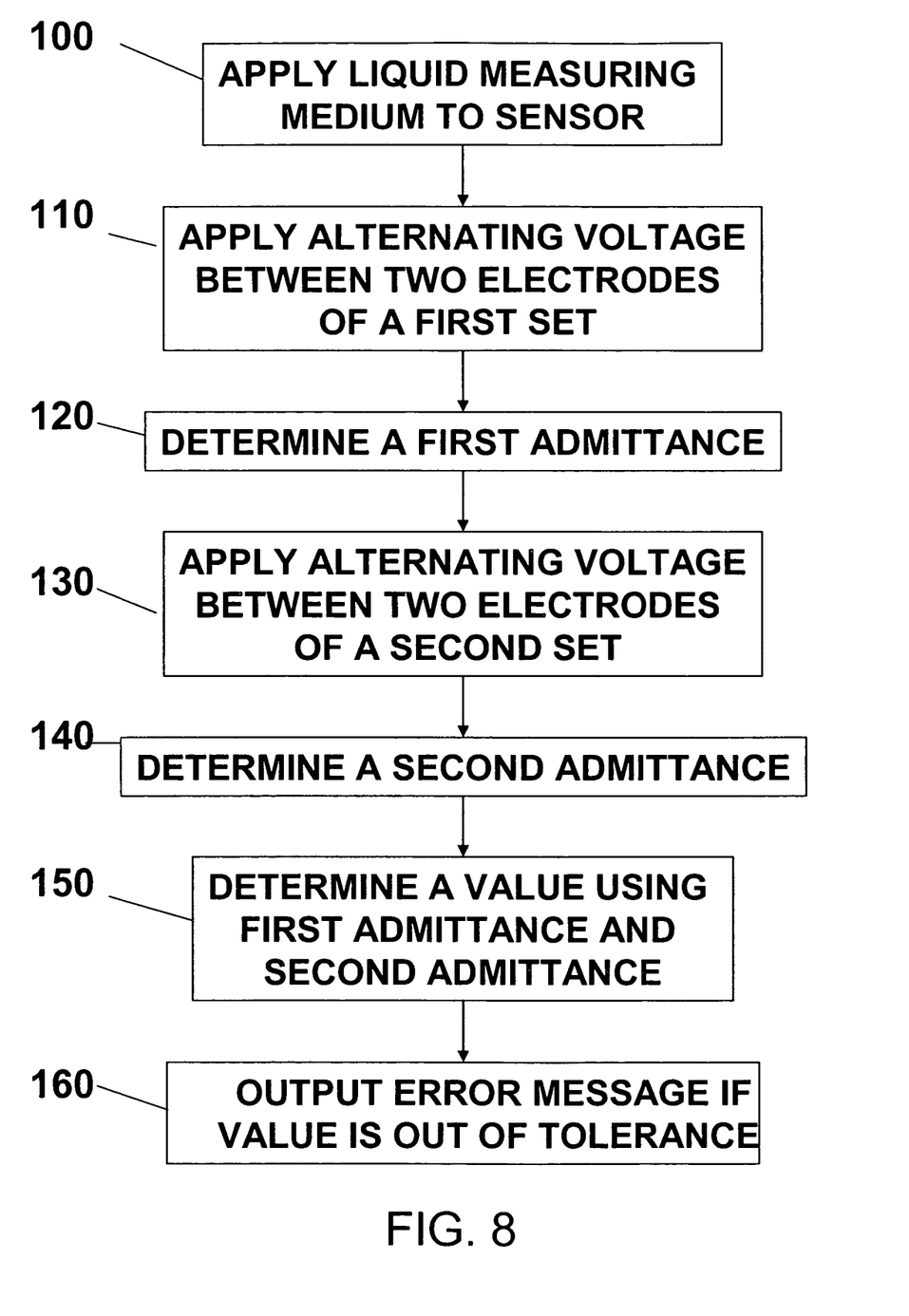
FIG. 8 is a process flow chart of one embodiment according to the present invention.

The present invention describes, inter alia, a method which enables the identification of deviations in the surface of the detection zone and thus prevents the generation of erroneous measured values. Referring to FIG. 8, after the measuring chamber has been filled with a liquid measuring medium in step 100, an alternating voltage is applied between two electrodes of a first set in step 110 and the alternating voltage conductivity (admittance) across the sample is measured in step 120 giving a first admittance. A sample liquid (e.g., a body fluid such as blood, serum, plasma, saliva etc.), an (aqueous) environmental sample, a process liquid, etc., an (aqueous) control, or a calibration liquid can be used as the liquid measuring medium.

Next in the process in one embodiment, subsequently, i.e., with a time lag, the alternating voltage is applied between two electrodes of a second set in step 130 and then the conductivity (admittance) between the second electrode pair is measured in step 140 giving a second admittance. The time lag between the two measurements is employed to detect changes in the wetted surface by incorporating. If the electrode surfaces are for example delimited by a glued on spacer, sample liquid may migrate under the spacer if it is not properly bonded. This enlargement of the wetted electrode surface which usually occurs slowly can be measured by measuring the conductivity at different times. Each set of electrodes consists of two electrodes. One of these electrodes can be a component of both sets. It is to be appreciated that the electrodes in electrode set 1 and electrode set 2 can also be identical. In another embodiment of process steps 110, 120, 130 and 140 may be carried out concurrently.

The electrodes are designed such that a change in the geometry of the measuring chamber or of the electrode geometry changes the size of the electrode surface that is wetted by the measuring medium and thus changes the magnitude of the measured conductivity. Since the conductivity depends not only on the geometry of the electrodes but also on the ion concentration of the measuring medium, the temperature etc., it is difficult to assess the quality of the measuring chamber by evaluating the measured absolute conductivity values. However, if a ratio is formed of the conductivities that were measured with both sets of electrodes, then it is possible to normalize to the geometric parameters. This is carried out in step 150.

The shape of the sensor to be measured is in principle unimportant for the method according to the present invention. The sensor can have any shape known to a person skilled in the art. For example the sensor can have an exposed electrode region that is directly contacted with the measuring medium (similar to the Accu-Chek® Advantage product from Roche Diagnostics) or it can have a capillary gap/channel above the electrode region (similar to the Accu-Chek® Aviva or Accu-Chek® Comfort Curve products from Roche Diagnostics). It is also possible to use sensors for flow measuring cells which have a sample channel above the electrode region (for example similar to the Roche OMNI® S product from Roche Diagnostics). However, a common feature of all sensors is that the electrochemically active surface of the electrodes of the sensor is determined by the shape of the electrodes and a dielectric (e.g., in the form of a cover, a spacer or a channel). The individual electrodes of the sensor can be manufactured from identical or different materials where the material as such is also not important for the invention within the scope of those materials which a person skilled in the field of electrochemical (bio)sensors would use and can be chosen as desired.

According to the invention the conductivity, i.e., the admittance, is determined by means of alternating current to check the electrochemical sensors. The admittance determined by means of high frequency, low-voltage alternating voltage is preferably used according to the invention. An alternating voltage frequency in the range of a few kilohertz, especially preferably in a range of 10 kHz has turned out to be particularly preferable. The alternating voltage should preferably be in the range of a few mV, in particular 8 mV.

In the method according to the invention the result of the check is outputted in step 160 after the assessment of the conductivity measurements especially when the check yields a result that deviates from the reference state (target value or target range). The result is typically displayed by means of a visually detectable display unit (e.g., lamp, light emitting diode, display, or by a printer). However, it is also possible in the case of a deviation from the reference state to output an acoustic signal (e.g., by a buzzer or loudspeaker) or a palpable signal (vibration). In this connection at least a deviation from the reference state (i.e., an error message) is typically outputted. It is, however, also possible to output a signal when the required state is reached. Furthermore, it is possible to identify measured values that were measured with sensors whose check results were outside of the target range e.g., when they are displayed, printed or stored. This is referred to as "flagging" such values.

Furthermore, the method according to the invention reliably prevents the use of aged or damaged system components. For example so-called parasitic resistances (parasitic contact resistance) are detected which result from contact resistances between test strips and connectors in a measuring instrument if, for example, the contacts are aged or the strips are scratched.

Compared to the measurement of direct voltage conductivity (conductance) the method according to the present invention and the corresponding system has the advantage that the test signal (i.e., the alternating voltage) is independent of an electrochemically detectable species. The mechanisms and system components for a haematocrit determination which is also based on alternating voltage conductivity are also checked and so-called parasitic contact resistances can be detected.

The invention is further elucidated on the basis of the following examples and FIGS. 2-6. Although the examples only elucidate the invention on the basis of coagulation sensors, the principle according to the invention can be readily applied to any type of electrochemical sensors such as enzyme sensors for determining metabolites such as glucose or lactate from blood samples.

The two sets of electrodes which were used for the method according to the invention in the following examples have the following composition:

Set 1: 1st electrode 14/2nd electrode 16
Set 2: 2nd electrode 16/3rd electrode 18

As already explained above it is sufficient, depending on the application, when two electrodes are measured at intervals. Thus, with only two electrodes, it is possible to detect whether sample liquid has migrated under the spacer 22. On the other hand, it is also possible to use the signals from more than three electrodes, i.e., to use two individual different electrodes per electrode set.

EXAMPLE 1

Checking Electrochemical Sensors

An alternating voltage (8 mV; 10 kHz) is applied for a period of 0.15 seconds to the electrode Set 1 of sensor 10 and the conductivity is measured. The signal that is determined is referred to as the first admittance (Ad1).

After a waiting time (1 second), an alternating voltage (8 mV; 10 kHz) is applied to the electrode Set 2 of sensor 10 for a period (3 seconds), and the conductivity is measured. The signal that is determined is referred to as the second admittance (Ad2).

The quotients of first admittance and second admittance (Ad2/Ad1) are determined as the so-called "failsafe admittance" signals.

EXAMPLE 2

Detection of Defective Coagulation Test Strips

Figure 2:
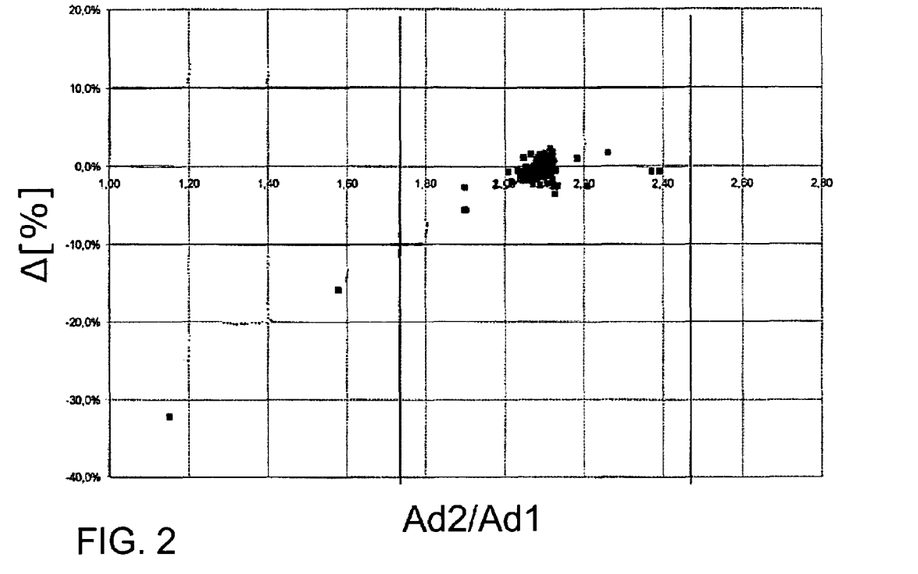
FIG. 2 shows a graph of the relationship between the relative deviation of the measuring result of an electrochemical blood coagulation sensor from the target value (rel. Δ in %; y axis) plotted against the quotient of two admittance measurements (Ad2/Ad1; so-called failsafe admittance, x axis).

The parameter "failsafe admittance" (Ad2/Ad1) for diverse coagulation test strips of Example 1 is plotted against the coagulation time measured with these test strips in FIG. 2.

A target range was defined for the failsafe admittance (vertical continuous lines). All test strips whose failsafe admittance was within the target range exhibit coagulation values within a very narrow window (+/−10%; horizontal continuous lines) around the mean value for the batch.

All test strips for which coagulation times are measured outside of the 10% window are detected as defective because they generate "failsafe admittance" signals which lie outside the "failsafe admittance" target range.

Seven experiments were run using seven test strips (see Table 2). Intact test strips were used in experiments 1 to 3 and 5 to 7. In experiment 4, a test strip was used whose working electrode had an active surface that was too small (for example because the electrodes were contaminated with residues of adhesive or because an air bubble got stuck in the

TABLE 1

Comparison of the admittance ratios for five exemplary test strips and the coagulation values that were measured with them.

| | | Admittance A $[10^{-4}]$ | | | Assessment | Coagulation time [s] | | | Assessment |
|---|---|---|---|---|---|---|---|---|---|
| Strip | Sample | A1 | A2 | A2/A1 | admittance | actual | target | rel. deviation | coagulation time |
| 1 | N1 | −3.93 | −4.52 | 1.151 | not OK | 8.60 | 12.69 | −32.2% | not OK |
| 2 | N2 | −3.93 | −7.47 | 1.899 | OK | 11.61 | 12.30 | −5.6% | OK |
| 3 | M1 | −3.92 | −6.19 | 1.579 | not OK | 21.07 | 25.04 | −15.8% | not OK |
| 4 | M2 | −3.86 | −7.34 | 1.900 | OK | 24.37 | 25.04 | −2.7% | OK |
| 5 | M3 | −3.93 | −8.57 | 2.182 | OK | 25.32 | 25.07 | 1.0% | OK |

As described in Example 1 the "failsafe admittance" signals are the quotients of two conductivity measurements (first admittance and second admittance). The individual values which form the basis of the above graph are compiled in Table 1 using five samples as an example. Samples N1 and N2 are normal donor blood, and samples M1, M2, and M3 are donor bloods containing the anticoagulation drug Marcumar® (dicumarol).

capillary channel above the electrodes). Currents that were too low were measured for these test strips. This result, in coagulation times that are too long.

TABLE 2

Comparison of the admittance ratios for seven exemplary test strips and the coagulation values that were measured with them.

| | Admittance A $[10^{-4}]$ | | | Assessment | Coagulation time [s] | | | Assessment |
|---|---|---|---|---|---|---|---|---|
| Strip | A1 | A2 | A2/A1 | admittance | actual | target | rel. deviation | coagulation time |
| 1 | 1.74 | 4.16 | 2.385 | OK | 16.8 | 16.8 | −0.4% | OK |
| 2 | 1.84 | 4.35 | 2.369 | OK | 16.2 | 16.8 | −3.6% | OK |
| 3 | 1.83 | 4.30 | 2.343 | OK | 16.7 | 16.8 | −0.7% | OK |
| 4 | 1.78 | 2.20 | 1.234 | not OK | 19.9 | 16.8 | 15.4% | not OK |
| 5 | 1.80 | 4.34 | 2.406 | OK | 16.8 | 16.8 | 0.1% | OK |
| 6 | 1.76 | 4.18 | 2.379 | OK | 16.8 | 16.8 | −0.4% | OK |
| 7 | 1.79 | 4.21 | 2.349 | OK | 17.5 | 16.8 | 4.0% | OK |

As shown in Table 2 the test strip whose working electrode had an active surface that was too small was detected as defective by the parameter "failsafe admittance".

EXAMPLE 3

Coagulation Test Strips with an Electrode Surface that is Too Small

Figure 3:
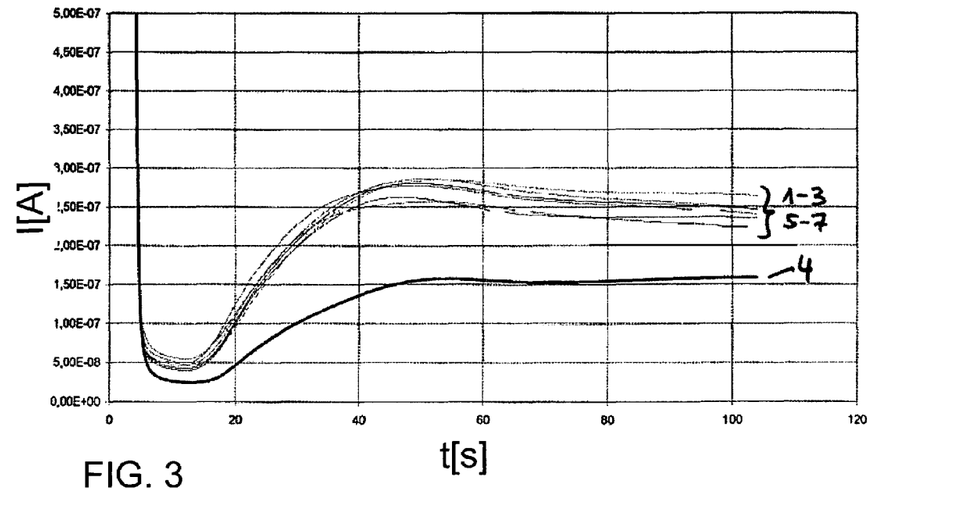
FIG. 3 shows the current/time curves (current I in amperes A plotted against the measuring time t in seconds s) for 7 blood coagulation measurements using 7 different sensors and in each case the same sample.

FIG. 3 shows current/time curves that are recorded when the measurement is carried out in an electrochemical coagulation sensor. For this purpose a direct voltage is applied between two electrodes in the measuring chamber of the strip and the time course of the current is measured.

EXAMPLE 4

Coagulation Test Strips with an Electrode Surface that is Too Large

Figure 4:
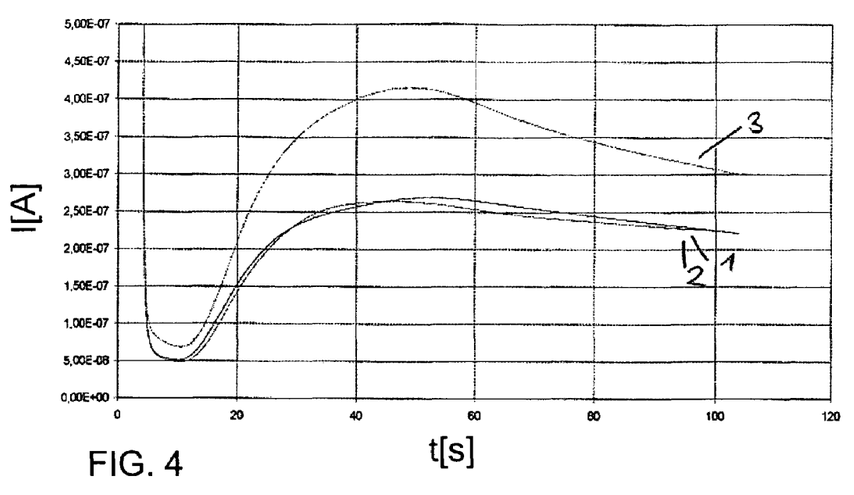
FIG. 4 shows the current/time curves (current I in amperes A plotted against the measuring time t in seconds s) for 3 blood coagulation measurements using 3 different sensors and in each case the same sample.

FIG. 4 shows current/time curves that were generated as described in Example 2.

Three experiments were run using three test strips (see Table 3). Intact test strips were used in experiments 1 and 2. A test strip was used in experiment 3 whose working electrode had an active surface that was too large as is observed for example when sample liquid migrates under a spacer which determines the working electrode geometry. Currents that were too high were measured for this test strip. This results in coagulation times that are too short.

As shown in Table 3 the test strip whose working electrode had an active surface that was too large was detected as defective by the parameter "failsafe admittance".

TABLE 3

Comparison of the admittance ratios for three exemplary test strips and the coagulation values that were measured with them.

| | Admittance A [$10^{-4}$] | | | Assessment | Coagulation time [s] | | | Assessment |
|---|---|---|---|---|---|---|---|---|
| Strip | A1 | A2 | A2/A1 | admittance | Actual | target | rel. deviation | coagulation time |
| 1 | 1.69 | 4.04 | 2.388 | OK | 17.2 | 17.0 | 1.0% | OK |
| 2 | 1.73 | 4.06 | 2.349 | OK | 16.9 | 17.0 | −0.9 | OK |
| 3 | 13.0 | 4.25 | 0.326 | not OK | 14.1 | 17.0 | −20.5% | not OK |

EXAMPLE 5

Influence of Parasitic Contact Resistances

Parasitic contact resistances that are, for example, caused by contact resistances between strips and connectors (aging of the contacts, scratching of the strips), can be detected by the method according to the invention and thus, erroneous measurements can be reliably prevented. This is demonstrated by FIGS. 5 and 6, as well as Table 4.

Figure 5:
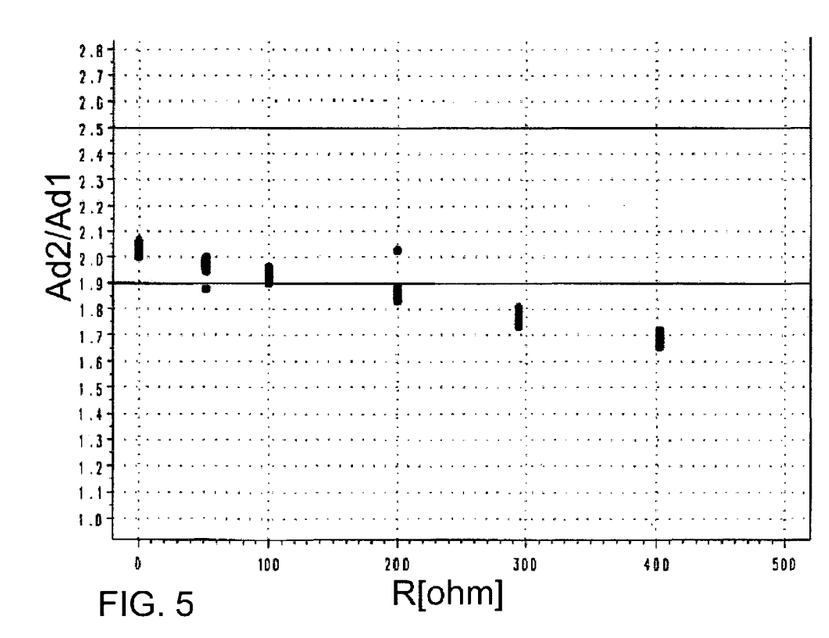
FIG. 5 shows a comparison of the so-called failsafe admittance (Ad2/Ad1, y axis) as a function of the contact resistance R (in ohm) between the connector (in the measuring instrument) and electrode contact (on a test strip).

In FIG. 5 the parameter "failsafe admittance" (Ad2/Ad1) for diverse coagulation test strips of example 1 is plotted against the contact resistances R (in ohm) between the connector (in the measuring instrument) and electrode contact (on the test strip) measured using these test strips and the associated measuring instruments. A target range was defined for the "failsafe admittance" (horizontal continuous lines), which in the illustrate example, is defined between 1.9 and 2.5.

Figure 6:
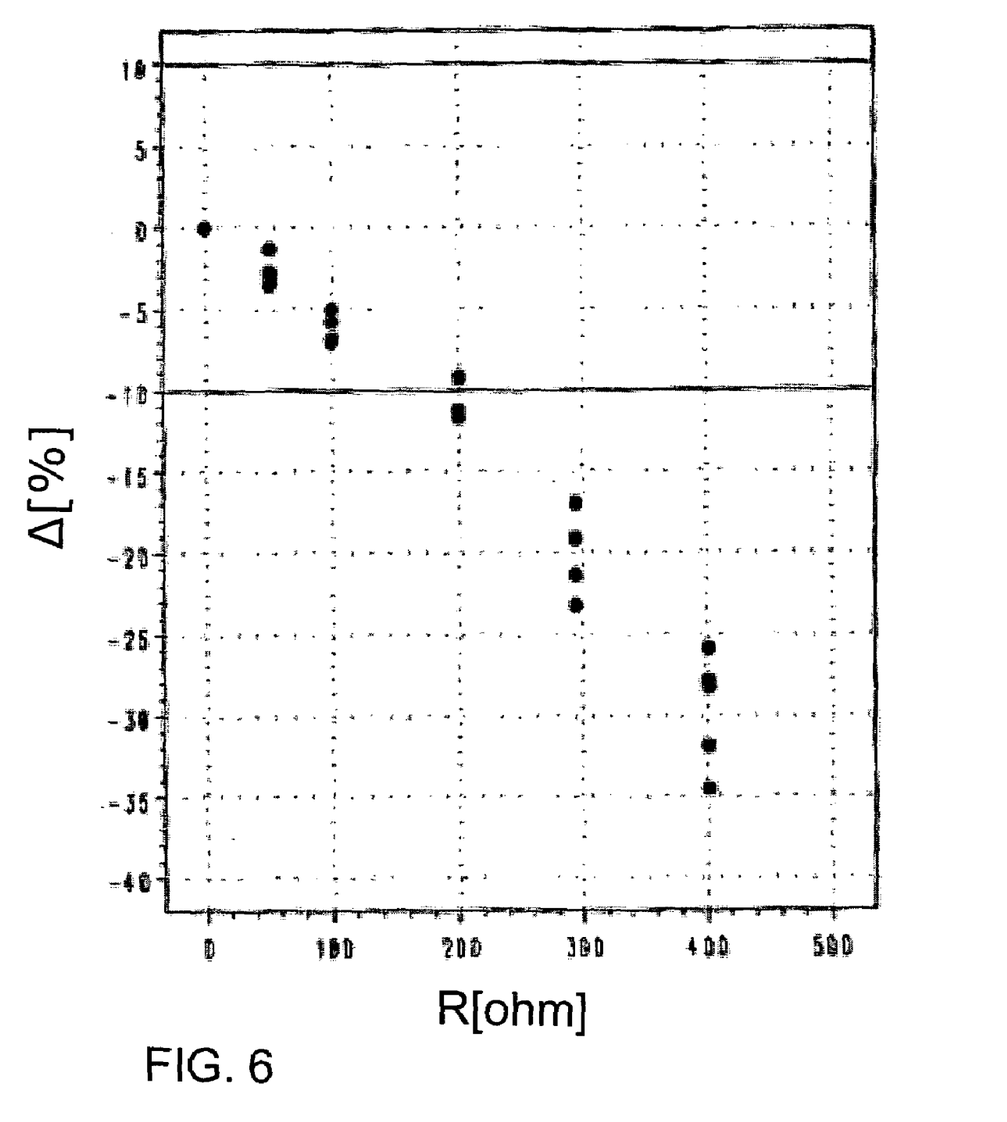
FIG. 6 shows the relationship between the relative deviation of the coagulation times (Δ in %) and the contact resistances R (in ohm) between the connector (in the measuring instrument) and electrode contact (on a test strip).

FIG. 6 shows the corresponding relative deviation of the coagulation times Δ (in %) as a function of the contact resistances R (in ohm) (similar to FIG. 5). The allowed tolerance of the coagulation time is in this case ±10% (relative deviation) (continuous horizontal lines).

The data of example 6 demonstrate that the use of damaged test strips or aged connectors in measuring instruments can be reliably excluded with the aid of the method according to the invention.

System Overview

Figure 7:
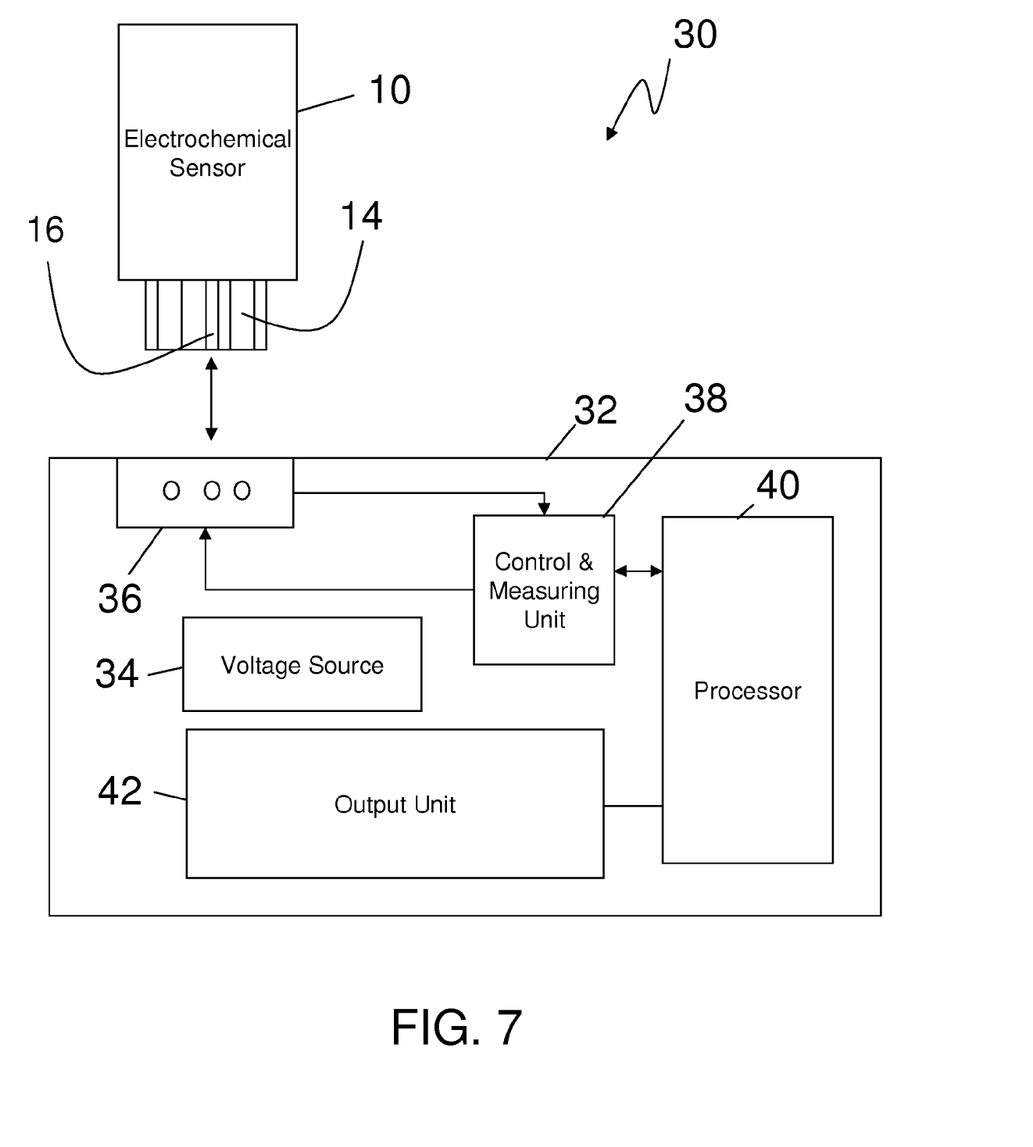
FIG. 7 shows a system for carrying out the method according to the invention comprising at least one electrochemical sensor with at least two electrodes and a measuring instrument according to the invention.

FIG. 7 shows a system, generally indicated by symbol 30, for carrying out the method according to the invention comprising at least one electrochemical sensor 10 with at least two electrodes 14, 16, such as depicted by FIG. 1E, and a measuring instrument 32 according to the invention. The measuring instrument 32 contains at least one source of alternating voltage 34 and contacts 36. The contacts 36 are for connecting to the electrodes 14, 16 of the sensor 10. The measuring instrument 32 also include control and measuring electronics 38 to generate test voltages on the contacts 36 and to detect the sensor signals (i.e., AD1 and AD2), and at least one processor 40 to compare and correlate the sensor signals on the basis of a program for carrying out the method according to the invention, such as the process shown by FIG. 8. The measuring instrument 32 further includes an output unit 42 (e.g., lamp, light emitting diode, display, data interface, printer, printer

TABLE 4

Measured values for FIGS. 5 and 6 as examples.

| R [ohm] | Admittance A [$10^{-4}$] | | | Assessment admittance | Coagulation time [s] | | | Assessment coagulation time |
|---|---|---|---|---|---|---|---|---|
| | A1 | A2 | A2/A1 | | actual | target | rel. deviation | |
| 0 | 2.90 | 5.88 | 2.03 | OK | 10.76 | 10.73 | 0.2% | OK |
| 51.8 | 2.88 | 5.74 | 1.99 | OK | 10.30 | 10.73 | −4.2% | OK |
| 100 | 2.88 | 5.65 | 1.96 | OK | 10.03 | 10.73 | −7.0% | OK |
| 200 | 2.86 | 5.33 | 1.87 | not OK | 9.55 | 10.73 | −12.4% | not OK |
| 294 | 2.90 | 5.17 | 1.78 | not OK | 8.61 | 10.73 | −24.7% | not OK |
| 402 | 2.90 | 4.96 | 1.71 | not OK | 7.86 | 10.73 | −36.5% | not OK |
| 0 | 2.96 | 5.96 | 2.01 | OK | 28.87 | 29.30 | −1.5% | OK |
| 51.8 | 2.96 | 5.88 | 1.99 | OK | 28.44 | 29.30 | −3.0% | OK |
| 100 | 2.98 | 5.73 | 1.93 | OK | 27.54 | 29.30 | −6.4% | OK |
| 200 | 2.93 | 5.43 | 1.85 | not OK | 25.70 | 29.30 | −14.0% | not OK |
| 294 | 2.97 | 5.24 | 1.76 | not OK | 23.08 | 29.30 | −26.9% | not OK |
| 402 | 3.01 | 5.00 | 1.66 | not OK | 19.92 | 29.30 | −47.1% | not OK | connection, etc.) for providing an error message when check results are outside of a predetermined target range.

The invention now being fully described, it will be apparent to one of ordinary skill in the art that many changes and modifications can be made thereto without departing from the spirit or scope of the appended claims.

What is claimed is:

1. A method for error checking an electrochemical sensor having at least two electrodes comprising:
   applying a liquid measuring medium to the electrodes;
   applying an alternating voltage to a first set of the electrodes of the sensor for a first period and measuring conductivity which is used to determine a first admittance;
   waiting a waiting time after said first period;
   after said waiting time, applying said alternating voltage to a second set of the electrodes of the sensor for a second period and measuring conductivity which is used to determine a second admittance;
   determining a value using said first admittance and said second admittance; and
   providing an error message if said value is out of tolerance.

2. The method according to claim 1 wherein said first set of electrodes and said second set of electrodes are the same.

3. The method according to claim 1 wherein one of said first set of electrodes is one of said second set of electrodes.

4. The method according to claim 1 wherein none of said first set of electrodes are in said second set of electrodes.

5. The method according to claim 1 further comprising determining whether an active electrode surface deviates from specified values based on said first admittance and said second admittance.

6. The method according to claim 1 further comprising determining whether an active electrode surface deviates from specified values based on said first admittance and said second admittance, and displaying an error message when the active electrode surface deviates from specified values.

7. The method according to claim 1, wherein an electrochemically active surface of the electrodes of the sensor is determined by the shape of the electrodes and a dielectric.

8. The method according to claim 1, wherein said first admittance and said second admittance are measured simultaneously.

9. The method according to claim 1, wherein said first admittance and said second admittance are measured successively.

10. The method according to claim 1, wherein said value is a ratio formed between said first and second admittances.

11. The method according to claim 1, wherein said alternating voltage applied to said electrodes has a voltage of about 8 mV and has a frequency of about 10 kHz.

12. The method according to claim 1, further comprising determining if a parasitic contact resistance is out of a predetermined tolerance.

13. The method according to claim 1, further comprising determining if a parasitic contact resistance is out of a predetermined tolerance, and displaying an error message when said parasitic contact resistance is out of said predetermined tolerance.

14. The method according to claim 1, wherein said alternating voltage is about 8 mV with a frequency of about 10 kHz, said first period is about 0.15 seconds, said waiting time is about 1 second, and said second period is about 3 seconds.

15. A method for error checking an electrochemical sensor having at least two electrodes comprising:
   applying a liquid measuring medium to the electrodes;
   applying an alternating voltage to the electrodes;
   determining a first admittance between a first set of electrodes of the sensor;
   determining a second admittance between a second set of electrodes of the sensor;
   determining a value using said first admittance and said second admittance;
   providing an error message if said value is out of tolerance; and
   determining if a parasitic contact resistance is out of a predetermined tolerance using a value in a target range correlated against a contact resistance between a connector in a measuring instrument checking said sensor and at least one of the electrodes of the sensor, and displaying an error message when said value is out of said predetermined tolerance for said contact resistance.

16. A method for error checking an electrochemical sensor having at least two electrodes comprising:
   applying a liquid measuring medium to the electrodes;
   applying an alternating voltage to the electrodes;
   determining a first admittance between a first set of electrodes of the sensor;
   determining a second admittance between a second set of electrodes of the sensor;
   determining a value using said first admittance and said second admittance;
   providing an error message if said value is out of tolerance; and
   determining if a parasitic contact resistance is out of a predetermined tolerance by making a relative deviation of a coagulation time as a function of contact resistance between a connector in a measuring instrument checking the sensor and at least one of the electrodes of the sensor, and displaying an error message if said relative deviation of the coagulation time is out of said predetermined tolerance for said contact resistance.

17. A measuring instrument for error checking an electrochemical sensor having at least two electrodes with a liquid measuring medium applied thereto, the instrument comprising:
   contacts which electrically connect to the electrodes of the sensor;
   electronics which generate test voltages and detect sensor signals from the electrodes;
   a processor programmed to:
      apply an alternating voltage to a first set of the electrodes of the sensor for a first period and measure conductivity which is used to determine a first admittance;
      wait a waiting time after said first period; and
      after said waiting time, apply said alternating voltage to a second set of the electrodes of the sensor for a second period and measure conductivity which is used to determine a second admittance;
      determine a value using said first admittance and said second admittance; and
      provide an error message if said value is out of tolerance; and
   an output unit which provides said error message.

18. A system comprising:
   at least one electrochemical sensor with at least two electrodes; and
   a measuring instrument for error checking said electrochemical sensor when having a liquid measuring medium applied thereto, said instrument having:
      contacts which electrically connect to the electrodes of the sensor,
      electronics which generate test voltages and detect sensor signals from the electrodes, a processor programmed to:
  apply an alternating voltage to a first set of the electrodes of the sensor for a first period and measure conductivity which is used to determine a first admittance;
  wait a waiting time after said first period; and
  after said waiting time, apply said alternating voltage to a second set of the electrodes of the sensor for a second period and measure conductivity which is used to determine a second admittance;
  determine a value using said first admittance and said second admittance; and
  provide an error message if said value is out of tolerance, and an output unit which provides said error message.

* * * * *